United States Patent
Yamazaki

(10) Patent No.: US 11,963,668 B2
(45) Date of Patent: Apr. 23, 2024

(54) ENDOSCOPE SYSTEM, PROCESSING APPARATUS, AND COLOR ENHANCEMENT METHOD

(71) Applicant: OLYMPUS CORPORATION, Tokyo (JP)

(72) Inventor: Kenji Yamazaki, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 57 days.

(21) Appl. No.: 17/940,328

(22) Filed: Sep. 8, 2022

(65) Prior Publication Data
US 2023/0000333 A1    Jan. 5, 2023

Related U.S. Application Data

(63) Continuation of application No. PCT/JP2020/011284, filed on Mar. 13, 2020.

(51) Int. Cl.
A61B 1/06    (2006.01)

(52) U.S. Cl.
CPC .......... *A61B 1/0655* (2022.02); *A61B 1/0638* (2013.01); *A61B 1/0661* (2013.01)

(58) Field of Classification Search
CPC ..... A61B 1/045; A61B 1/0638; A61B 1/0655; A61B 1/0661
USPC .......... 348/618, 45, 65, 222.1, 223.1, 225.1, 348/231.6, 235, 256, 253, 242
See application file for complete search history.

(56) References Cited

U.S. PATENT DOCUMENTS

| 2011/0234782 A1 | 9/2011 | Ehrhardt et al. |
| 2018/0289240 A1 | 10/2018 | Aoyama |
| 2019/0021580 A1 | 1/2019 | Mishima |

(Continued)

FOREIGN PATENT DOCUMENTS

| EP | 2 371 265 A2 | 10/2011 |
| EP | 3 395 230 A1 | 10/2018 |
| EP | 3 437 542 A1 | 2/2019 |

(Continued)

OTHER PUBLICATIONS

International Search Report dated Jun. 2, 2020 received in PCT/JP2020/011284.

*Primary Examiner* — Sherrie Hsia
(74) *Attorney, Agent, or Firm* — Scully, Scott, Murphy & Presser, P.C.

(57) ABSTRACT

An endoscope system includes a light source apparatus configured to cause light of a plurality of colors to be emitted at a first/second light amount ratio to generate first/second illumination light, an endoscope configured to generate an image pickup signal, and a processing apparatus including a processor. The processor causes the light source apparatus to emit light while switching light between the first/second illumination light, generates a first image signal from an image pickup signal related to the first illumination light, generates a second image signal from an image pickup signal related to the second illumination light and generates a corrected image signal in which color is enhanced based on the first and the second image signals. The second illumination light is light obtained by adjusting the second light amount ratio so that the second image signal related to a reference portion substantially indicates achromatic color.

16 Claims, 9 Drawing Sheets

(56) References Cited

U.S. PATENT DOCUMENTS

2019/0159687 A1* 5/2019 Kubo .................. A61B 1/045

FOREIGN PATENT DOCUMENTS

| | | |
|---|---|---|
| JP | 2000-014629 A | 1/2000 |
| JP | 3228627 B2 | 11/2001 |
| JP | 2013-000176 A | 1/2013 |
| JP | 2016-007355 A | 1/2016 |
| JP | 6050286 B2 | 12/2016 |
| JP | 2017-136405 A | 8/2017 |
| JP | 2017-158929 A | 9/2017 |
| JP | 6439083 B1 | 12/2018 |
| WO | 2016/006371 A1 | 1/2016 |
| WO | 2016/117112 A1 | 7/2016 |
| WO | 2017/110334 A1 | 6/2017 |
| WO | 2017/170233 A1 | 10/2017 |

* cited by examiner

FIG. 6

| | VIOLET LED | BLUE LED | GREEN LED | RED LED |
|---|---|---|---|---|
| WL | $\alpha wv \times Gw$ | $\alpha wb \times Gw$ | $Gw$ | $\alpha wr \times Gw$ |
| CE | $\alpha wv \times Gw \times Kv$ | $\alpha wb \times Gw \times Kb$ | $Gw \times Kg$ | $\alpha wr \times Gw \times Kr$ |

FIG. 7

| | VIOLET LED | BLUE LED | GREEN LED | RED LED |
|---|---|---|---|---|
| WL | $\alpha wv \times Gw$ | $\alpha wb \times Gw$ | $Gw$ | $\alpha wr \times Gw$ |
| FIRST CE | $\alpha wv \times Gw \times Kv1$ | $\alpha wb \times Gw \times Kb1$ | $Gw$ | $\alpha wr \times Gw \times Kr1$ |
| SECOND CE | $\alpha wv \times Gw \times Kv2$ | $\alpha wb \times Gw \times Kb2$ | $Gw$ | $\alpha wr \times Gw \times Kr2$ |
| THIRD CE | $\alpha wv \times Gw \times Kv3$ | $\alpha wb \times Gw \times Kb3$ | $Gw$ | $\alpha wr \times Gw \times Kr3$ |

FIG. 8

|  | NEAR DISTANCE | MEDIUM DISTANCE | FAR DISTANCE |
|---|---|---|---|
| FIRST PORTION | Kc1n | Kc1m | Kc1f |
| SECOND PORTION | Kc2n | Kc2m | Kc2f |
| THIRD PORTION | Kc3n | Kc3m | Kc3f |

FIG. 9

|  | VIOLET LED | GREEN LED |
|---|---|---|
| NBI | $\alpha Nv \times GN$ | GN |
| FIRST CE | $\alpha Nv \times GN \times Kv1$ | GN |
| SECOND CE | $\alpha Nv \times GN \times Kv2$ | GN |
| THIRD CE | $\alpha Nv \times GN \times Kv3$ | GN |

ENDOSCOPE SYSTEM, PROCESSING APPARATUS, AND COLOR ENHANCEMENT METHOD

CROSS REFERENCE TO RELATED APPLICATION

This application is a continuation application of PCT/JP2020/011284 filed on Mar. 13, 2020, the entire contents of which are incorporated herein by this reference.

BACKGROUND OF THE INVENTION

1. Field of the Invention

The present invention relates to an endoscope system, a processing apparatus, and a color enhancement method for performing color enhancement on an image acquired by emitting a plurality of kinds of light having different center wavelengths.

2. Description of the Related Art

In related art, an endoscope apparatus that displays an image in which superficial blood vessels and superficial microstructures are made clear has been proposed and has greatly contributed to diagnosis of an affected area.

For example, Japanese Patent Application Laid-Open Publication No. 2013-176 discloses a technique of acquiring a normal light image by picking up a subject image in which light amount values of B light, G light and R light are equal, acquiring a special light image by picking up a subject image in which light amount values of B light, G light and R light are B light >G light >R light and synthesizing the special light image and the normal light image to obtain a synthesized image in which superficial microscopic blood vessels, and the like, are made clear.

Further, for example, Japanese Patent No. 6050286 discloses a technique of, in a feature space formed with a plurality of pieces of color information, generating an image in which a difference in color between a normal portion and an abnormal portion is enhanced by moving coordinates of first to third ranges in which an observation target within a subject is distributed to cause a coordinate of one specific range among the first to the third ranges to fall within a reference range and moving the two ranges other than the specific range so as to be separate from each other.

Further, for example, Japanese Patent No. 3228627 discloses an IHb color enhancement technique of calculating a hemoglobin concentration (IHb) and an average value <IHb> of IHb and enhancing a gap of IHb from the average value <IHb>.

SUMMARY OF THE INVENTION

An endoscope system according to one aspect of the present invention includes an endoscope, a light source apparatus, and a processing apparatus, in which the light source apparatus includes a plurality of semiconductor light emitting devices configured to emit light with different center wavelengths and causes the plurality of semiconductor light emitting devices to emit light at a certain light amount ratio to generate illumination light, the endoscope includes an image pickup device configured to pick up an image of return light from a subject irradiated with the illumination light to generate an image pickup signal having a plurality of color components, the processing apparatus includes a processor, the processor is configured to execute: controlling the light source apparatus to switch light between first illumination light emitted at a first light amount ratio and second illumination light emitted at a second light amount ratio different from the first light amount ratio, generating a first image signal based on an image pickup signal obtained by picking up an image of a subject illuminated with the first illumination light, generating a second image signal based on an image pickup signal obtained by picking up an image of the subject illuminated with the second illumination light, and generating a corrected image signal in which color is enhanced based on the first image signal and the second image signal, and the second illumination light is light obtained by adjusting the second light amount ratio so that the second image signal related to a reference portion of the subject indicates achromatic color within a predetermined error range.

A processing apparatus according to one aspect of the present invention includes a processor, in which the processor is configured to execute: controlling a light source apparatus to switch light between first illumination light in which a plurality of kinds of light with different center wavelengths are emitted at a first light amount ratio and second illumination light in which the plurality of kinds of light are emitted at a second light amount ratio different from the first light amount ratio, generating a first image signal based on an image pickup signal obtained by picking up an image of a subject illuminated with the first illumination light, generating a second image signal based on an image pickup signal obtained by picking up an image of the subject illuminated with the second illumination light, and generating a corrected image signal in which color is enhanced based on the first image signal and the second image signal, and the second illumination light is light obtained by adjusting the second light amount ratio so that the second image signal related to a reference portion of the subject indicates achromatic color within a predetermined error range.

A color enhancement method according to one aspect of the present invention includes emitting light while switching light between first illumination light in which a light amount ratio of a plurality of kinds of light with different center wavelengths is set at a first light amount ratio and second illumination light in which the light amount ratio is set at a second light amount ratio different from the first light amount ratio, generating a first image signal based on an image pickup signal obtained by picking up an image of a subject illuminated with the first illumination light, generating a second image signal based on an image pickup signal obtained by picking up an image of the subject illuminated with the second illumination light, generating a corrected image signal in which color is enhanced based on the first image signal and the second image signal, and adjusting the second light amount ratio so that the second image signal related to a reference portion of the subject indicates achromatic color within a predetermined error range.

BRIEF DESCRIPTION OF THE DRAWINGS

FIG. 6 is a table indicating setting examples of light amounts of respective LEDs in first illumination light and second illumination light when the color enhancement mode is ON in a normal observation mode according to the first embodiment;

FIG. 7 is a table indicating an example of the normal observation mode in which a light amount ratio of the respective LEDs in the second illumination light is made different in accordance with a portion of a subject according to the first embodiment;

FIG. 8 is a table indicating an example of the normal observation mode in which the light amount ratio of the respective LEDs in the second illumination light is made different in accordance with the portion of the subject and a distance from a distal end portion of an endoscope to the portion of the subject according to the first embodiment;

FIG. 9 is a table indicating an example of an NBI observation mode in which a light amount ratio of a violet LED and a green LED in the second illumination light is made different in accordance with the portion of the subject according to the first embodiment:

DETAILED DESCRIPTION OF THE PREFERRED EMBODIMENTS

Figure 1:
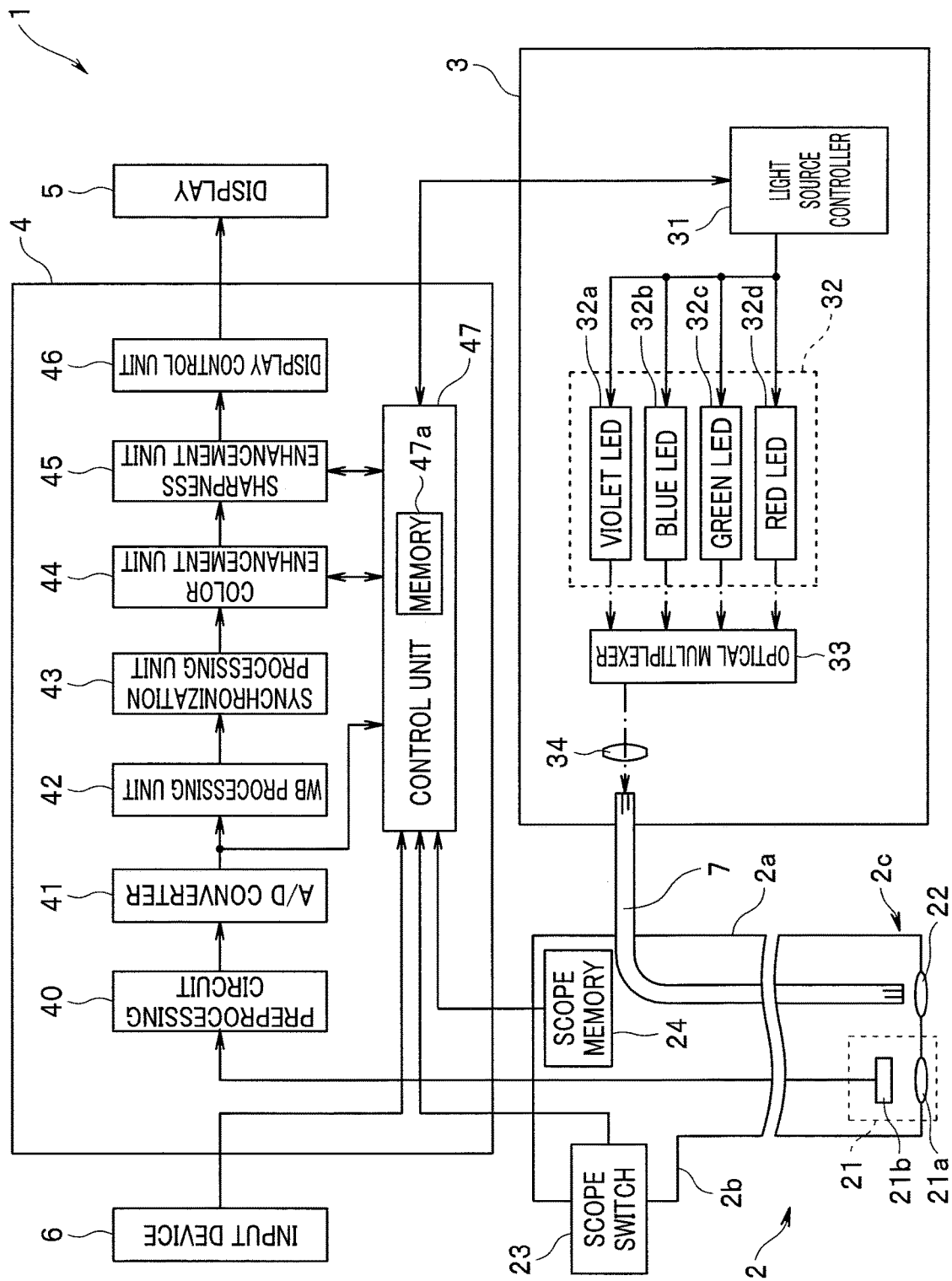
FIG. 1 is a view illustrating a configuration of an endoscope apparatus according to a first embodiment of the present invention.

An embodiment of the present invention will be described below with reference to the drawings. However, the present invention is not limited to the embodiment described below.

Note that the same reference numerals will be assigned to the same or corresponding components as appropriate in the drawings. Further, the drawings are schematic drawings, and there is a case where a relationship of lengths of respective components, a ratio of lengths of respective components, and the like, in one drawing are different from an actual relationship, ratio, and the like. Further, there is a case where part of a relationship and a ratio of lengths are different among a plurality of drawings.

First Embodiment

FIG. 1 to FIG. 13 illustrate a first embodiment of the present invention, and FIG. 1 is a view illustrating a configuration of an endoscope apparatus 1.

The endoscope apparatus 1 (endoscope system) includes an endoscope 2, a light source apparatus 3, a processor 4 (processing apparatus), a display 5 and an input device 6.

The endoscope 2 is configured as an electronic endoscope that can be inserted into a body cavity or the like of a subject, and picks up an image of body tissues or the like of the subject and outputs an image pickup signal.

The light source apparatus 3 supplies illumination light to the endoscope 2 so as to enable observation of the subject in a dark portion.

The processor 4, which is connected to the light source apparatus 3 and the endoscope 2, generates and outputs a video signal for observation and/or for recording based on the image pickup signal outputted from the endoscope 2.

The display 5, which includes a display device such as an LCD (liquid-crystal display) and an organic EL (electroluminescence) display, displays an observation image, and the like, in accordance with the video signal outputted from the processor 4.

The input device 6, which includes an operation member such as a switch and a button, outputs to the processor 4, an instruction signal in accordance with operation inputted by a user such as a surgeon.

The endoscope 2 is, for example, detachably connected to the processor 4 by way of a universal cord (not illustrated) and detachably connected to the light source apparatus 3 by way of a light guide cable (not illustrated).

The endoscope 2 includes an elongated insertion portion 2a that can be inserted into the subject, and an operation portion 2b provided on a proximal end side of the insertion portion 2a.

An image pickup unit 21 and an illumination optical system 22 are provided at a distal end portion 2c of the insertion portion 2a.

A light guide 7 for transmitting illumination light passes through and is disposed inside the light guide cable and the endoscope 2 described above. An emission end portion of the light guide 7 is disposed at a position facing the illumination optical system 22. By this means, the illumination light transmitted by way of the light guide 7 is emitted toward the subject by the illumination optical system 22.

The image pickup unit 21 includes an objective optical system 21a and an image pickup device 21b.

The objective optical system 21a forms an image of return light from the subject illuminated with the illumination light emitted from the illumination optical system 22, on the image pickup device 21b.

The image pickup device 21b picks up an optical image of the subject formed by the objective optical system 21a to generate an image pickup signal including a plurality of color components and outputs the generated image pickup signal.

Specifically, the image pickup device 21b is configured as an image sensor such as a CCD and a CMOS in which a plurality of pixels are arranged in a matrix, and, which includes, for example, color filters of a Bayer array of primary colors (which may be, for example, color filters of complementary colors).

The operation portion 2b is formed in a shape that can be grasped and operated by the user, and a scope switch 23 and a scope memory 24 are provided.

The scope switch 23, which includes an operation member such as a switch and a button, outputs to the processor 4, an instruction signal in accordance with operation inputted by the user.

The scope memory 24 stores endoscope information including information specific to the endoscope 2, such as an ID number of the endoscope 2 and spectral sensitivity characteristic information of the image pickup unit 21.

A signal line to be connected to the image pickup device 21b, a signal line to be connected to the scope switch 23, and a signal line to be connected to the scope memory 24 are disposed inside the endoscope 2 and inside the universal cable described above and are electrically connected to the processor 4 by way of the universal cable.

This allows the endoscope information stored in the scope memory 24 to be read by a control unit 47 which will be described later, of the processor 4 when the endoscope 2 and the processor 4 are electrically connected and the processor 4 is powered on. Further, the instruction signal outputted from the scope switch 23 is transmitted to the control unit 47. Still further, the image pickup signal outputted from the image pickup device 21b is transmitted to a preprocessing circuit 40 which will be described later, inside the processor 4.

The light source apparatus 3 includes a light source controller 31, a light source unit 32, an optical multiplexer 33, and a condenser lens 34.

The light source controller 31, which includes a control circuit and the like, controls light emission by the light source unit 32 in accordance with an illumination control signal outputted from the processor 4.

The light source unit 32, which functions as a light source section and includes a plurality of semiconductor light emitting devices (specifically. LEDs 32a to 32d described below) that emit light with different center wavelengths, causes the plurality of semiconductor light emitting devices to emit light at a certain light amount ratio to generate illumination light.

Specifically, the light source unit 32 includes, for example, a violet LED (light-emitting diode) 32a, a blue LED 32b, a green LED 32c and a red LED 32d.

The violet LED 32a emits violet light (hereinafter, also referred to as V light) having a center wavelength belonging to a violet region. Particularly, the present embodiment assumes an endoscope system capable of implementing an NBI observation mode, and thus, it is assumed that the violet LED 32a emits violet light in a narrow band of a wavelength from 390 to 445 (nm).

The blue LED 32b emits blue light (hereinafter, also referred to as B light) having a center wavelength belonging to a blue region. As will be described later, the blue light is also preferably light in a narrow band.

The green LED 32c emits green light (hereinafter, also referred to as G light) having a center wavelength belonging to a green region. As described above, the present embodiment assumes the NBI observation mode, and thus, it is assumed that the green LED 32c emits green light in a narrow band of a wavelength from 530 to 550 (nm).

The red LED 32d emits red light (hereinafter, also referred to as R light) having a center wavelength belonging to a red region. As will be described later, the red light is also preferably light in a narrow band.

The respective LEDs 32a to 32d of the light source unit 32 individually emit light or perform extinction at the respective light amounts based on control by the light source controller 31. Note that the light amounts described here refer to light amounts of illumination light emitted during a period while an image is picked up (exposed) by the image pickup device 21b.

Note that there are various spectral sensitivity characteristics of the image pickup unit 21 indicated by the spectral sensitivity characteristic information stored in the scope memory 24 in accordance with models (further, individuals) of the endoscope 2. For example, wavelength bands of light received by the image pickup device 21b by way of an R (red) filter, a G (green) filter and a B (blue) filter of a Bayer array of primary colors are not respectively limited to a red wavelength band, a green wavelength band and a blue wavelength band, and the image pickup device 21b may be actually sensitive to a broader bandwidth.

Thus, as a light source to be employed as the light source unit 32 that accurately controls illumination light, it is preferable to use a light source, for which a band is made narrower, and for which optical spectra of respective kinds of color light are discrete.

For example, also in a case where an LED is used as a light source of the light source unit 32, it is preferable to use an LED of a type that generates light emission color with light emitted from the LED itself rather than use an LED of a type that generates light emission color with a fluorescence agent.

Further, as well as an LED, for example, a laser light source such as a semiconductor laser (LD: laser diode) may be used as the light source of the light source unit 32.

This can reduce color mixture upon image pickup by way of primary color filters and can improve accuracy of color enhancement.

The optical multiplexer 33 multiplexes light emitted from the respective LEDs 32a to 32d of the light source unit 32 and emits the multiplexed light.

The condenser lens 34 condenses light emitted from the optical multiplexer 33 to the emission end portion of the light guide 7.

The processor 4 includes the preprocessing circuit 40, an A/D converter 41, a WB (white balance) processing unit 42, a synchronization processing unit 43, a color enhancement unit 44, a sharpness enhancement unit 45, a display control unit 46 and a control unit 47. The preprocessing circuit 40 that is disposed before the A/D converter 41 is an analog circuit. Further, the WB processing unit 42, the synchronization processing unit 43, the color enhancement unit 44, the sharpness enhancement unit 45 and the display control unit 46 that are disposed subsequent to the A/D converter 41 are digital circuits, and, further, the control unit 47 is also a digital circuit.

It is assumed here that digital circuit units of the processor 4 are configured to implement functions of the respective units by, for example, a processor such as an ASIC (application specific integrated circuit) and an FPGA (field programmable gate array) including a CPU (central processing unit), and the like, reading and executing a processing program stored in a storage apparatus (or a recording medium) such as a memory.

However, the digital circuit units are not limited to this, and the respective units of the processor 4 may be configured as, for example, dedicated electronic circuits that implement the respective functions.

The preprocessing circuit 40 amplifies the image pickup signal outputted from the image pickup unit 21 of the endoscope 2 and, further, for example, performs noise removal processing such as correlated double sampling.

The A/D converter 41 performs A/D conversion on the analog image pickup signal outputted from the preprocessing circuit 40 to generate a digital image signal. The digital image signal generated by the A/D converter 41 is outputted to the WB processing unit 42 and the control unit 47.

The WB processing unit 42 performs white balance processing on the image signal having a plurality of color components, outputted from the A/D converter 41.

The synchronization processing unit 43 performs synchronization processing (also referred to as demosaicking processing) on the image signal having a plurality of color components, outputted from the A/D converter 41. In other words, in a case where the image pickup device 21b is, for example, a single-chip image pickup device including color filters of a Bayer array of primary colors as described above, the image pickup signal becomes a signal having one color component in one pixel. Thus, for example, in a case of a G pixel in which a G filter is provided, the synchronization processing unit 43 performs synchronization processing of generating RGB components at a pixel position of the G pixel by supplementing a lacking R component and B component at the position of the G pixel in a pixel signal based on an R component in a surrounding R pixel and a B component in a surrounding B pixel. An image signal in which RGB components exist at the respective pixel positions is generated by also performing synchronization processing on pixels in which other color filters are provided in a similar manner.

The color enhancement unit 44 performs color enhancement processing on the image signal outputted from the synchronization processing unit 43 based on control by the control unit 47. The color enhancement processing to be performed by the color enhancement unit 44 will be described in detail later.

The sharpness enhancement unit 45 performs sharpness enhancement processing on the image signal outputted from the color enhancement unit 44 based on control by the control unit 47.

The display control unit 46 generates a video signal in which the image signal outputted from the sharpness enhancement unit 45 is allocated to an R channel, a G channel and a B channel of the display 5 and outputs the generated video signal to the display 5.

The control unit 47 is a controller that comprehensively controls the whole of the endoscope apparatus 1 including the processor 4 by receiving instruction signals outputted from the input device 6 and the scope switch 23.

The control unit 47 includes a memory 47a that stores a processing program to be executed by the control unit 47.

Further, in the memory 47a, information such as a color adjustment coefficient for adjusting light amounts of the respective LEDs 32a to 32d in accordance with a type of the illumination light and an enhancement coefficient to be used in color enhancement processing to be performed by the color enhancement unit 44 is stored in advance.

Note that while both the color adjustment coefficient and the enhancement coefficient are stored in the memory 47a here, at least one of the color adjustment coefficient or the enhancement coefficient may be stored in a memory (not illustrated) in the light source controller 31.

As described above, the control unit 47 reads the endoscope information stored in the scope memory 24 when the endoscope 2 and the processor 4 are electrically connected and the processor 4 is powered on.

Then, the control unit 47 sets an observation mode of the endoscope apparatus 1 based on an instruction signal outputted from an observation mode switch (not illustrated) provided at the input device 6 and/or the scope switch 23. It is assumed here that an observation mode that can be set at the endoscope apparatus 1 includes, for example, a normal observation mode and a special light observation mode. Note that while in the present embodiment, an NBI (narrow-band imaging) observation mode will be described as an example of the special light observation mode, the special light observation mode is not limited to the NBI observation mode.

Further, the control unit 47 sets ON/OFF of a color enhancement mode of the endoscope apparatus 1 based on an instruction signal outputted from a color enhancement mode setting switch (not illustrated) provided at the input device 6 and/or the scope switch 23.

In other words, the endoscope apparatus 1 of the present embodiment can set ON/OFF of the color enhancement mode in each observation mode. It is therefore possible to select and set one of ON of the color enhancement mode in the normal observation mode, OFF of the color enhancement mode in the normal observation mode, ON of the color enhancement mode in the NBI observation mode or OFF of the color enhancement mode in the NBI observation mode.

The control unit 47 generates an illumination control signal for causing the light source apparatus 3 to emit illumination light appropriate for the set observation mode and the set ON/OFF of the color enhancement mode in accordance with the spectral sensitivity characteristic information of the image pickup unit 21 indicated by the endoscope information read from the scope memory 24 and outputs the illumination control signal to the light source controller 31.

In a case where the color enhancement mode is ON, the control unit 47 controls the light source apparatus 3 to emit light while switching light between first illumination light in which a light amount ratio of the respective LEDs 32a to 32d is set at a first light amount ratio for observing the subject and second illumination light in which the light amount ratio is set at a second light amount ratio different from the first light amount ratio.

On the other hand, in a case where the color enhancement mode is OFF, the control unit 47 controls the light source apparatus 3 to emit the first illumination light for observing the subject.

If an image of return light from the subject irradiated with the illumination light emitted from the light source apparatus 3 is picked up by the image pickup unit 21, the control unit 47 extracts brightness information of the subject from the image signal outputted from the A/D converter 41, generates an illumination control signal so as to make the brightness of the subject appropriate based on current brightness information and outputs the illumination control signal to the light source controller 31.

Further, in a case where the color enhancement mode is ON, the control unit 47 reads the enhancement coefficient from the memory 47a and controls the color enhancement unit 44 to perform color enhancement processing using the read enhancement coefficient.

Figure 2:
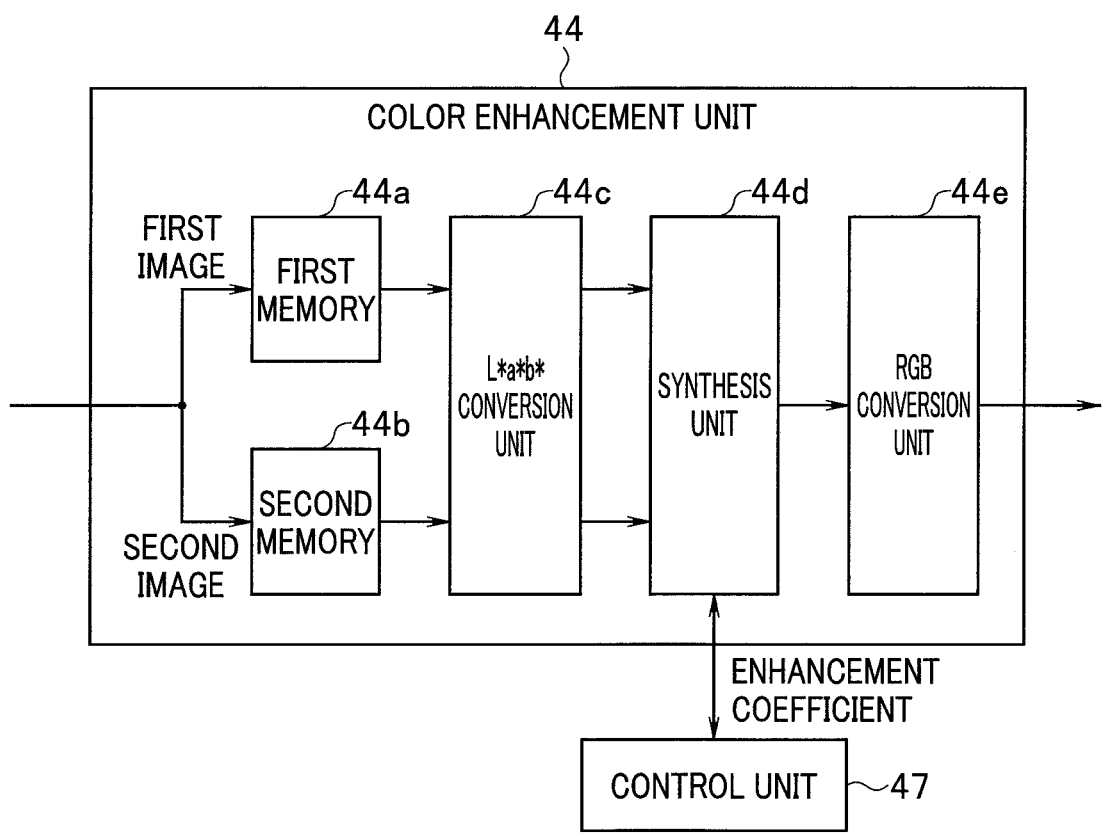
FIG. 2 is a block diagram illustrating a configuration of a color enhancement unit according to the first embodiment.

FIG. 2 is a block diagram illustrating a configuration of the color enhancement unit 44.

The color enhancement unit 44 includes a first memory 44a, a second memory 44b, an L*a*b* conversion unit 44c, a synthesis unit 44d and an RGB conversion unit 44e.

The first memory 44a is a memory that stores a first image signal obtained by processing a first image pickup signal generated by picking up an image of return light from the subject irradiated with the first illumination light. Here, the first illumination light is illumination light in which a light amount ratio of the respective LEDs 32a to 32d is set at a first light amount ratio for observing the subject. Specific examples of the first illumination light include white light WL in the normal observation mode, NBI illumination light in the NBI observation mode, and the like.

The second memory 44b is a memory that stores a second image signal obtained by processing a second image pickup signal generated by picking up an image of return light from the subject irradiated with the second illumination light. Here, the second illumination light is illumination light emitted at a second light amount ratio different from the first light amount ratio using the respective LEDs 32a to 32d that are the same as the LEDs emitting the first illumination light.

The second illumination light, which is also referred to as color enhancement light CE (color enhance), is light for which the second light amount ratio is adjusted so that a second image signal related to a reference portion of the subject indicates achromatic color within a predetermined error range (in examples in some color spaces, in a case of an RGB color space, R=G=B. CIE (International Commission on Illumination), (hereinafter, "CIE" will be omitted), in a case of an L*a*b* color space, a*=b*=0, and the like).

Here, examples of the reference portion of the subject include a normal portion in the subject (for example, a normal tissue such as normal mucosa), which does not contain a blood vessel. Further, a biological model may be used as the reference portion of the subject. Thus, in the second image signal, the reference portion of the subject is indicated in achromatic color (gray scale such as white color) and color occurs at an abnormal portion, and the like, other than the reference portion.

The L*a*b* conversion unit 44c reads the first image signal (it is assumed that the RGB component is (R1, G1, B1)) of an RGB color space stored in the first memory 44a and converts the first image signal into a first image signal (L1*, a1*, b1*) of an L*a*b* color space.

Further, the L*a*b* conversion unit 44c reads the second image signal (it is assumed that the RGB component is (R2, G2, B2)) of the RGB color space stored in the second memory 44b and converts the second image signal into a second image signal (L2*, a2*, b2*) of the L*a*b* color space.

The synthesis unit 44d generates a corrected image signal by performing color enhancement on the first image signal (L1*, a1*, b1*) based on the second image signal (L2*, a2*, b2*). When the synthesis unit 44d synthesizes the image signals, the enhancement coefficient transmitted from the control unit 47 is used as will be described later.

Figure 4:
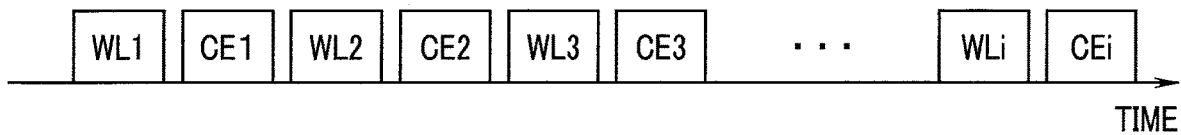
FIG. 4 is a timing chart indicating an aspect where white light WL and color enhancement light CE are alternately emitted when a color enhancement mode is ON according to the first embodiment.

Note that the first image pickup signal and the second image pickup signal are signals acquired through image pickup at different time points (see FIG. 4, and the like). Thus, the synthesis unit 44d preferably performs synthesis after processing of adjusting positions of the first image signal (L1*, a1*, b1*) and the second image signal (L2*, a2*, b2*). This can reduce image blurring and color shift due to misalignment.

The RGB conversion unit 44e converts the signal of the L*a*b* color space subjected to synthesis by the synthesis unit 44d into a signal of the RGB color space and outputs the signal.

Figure 3:
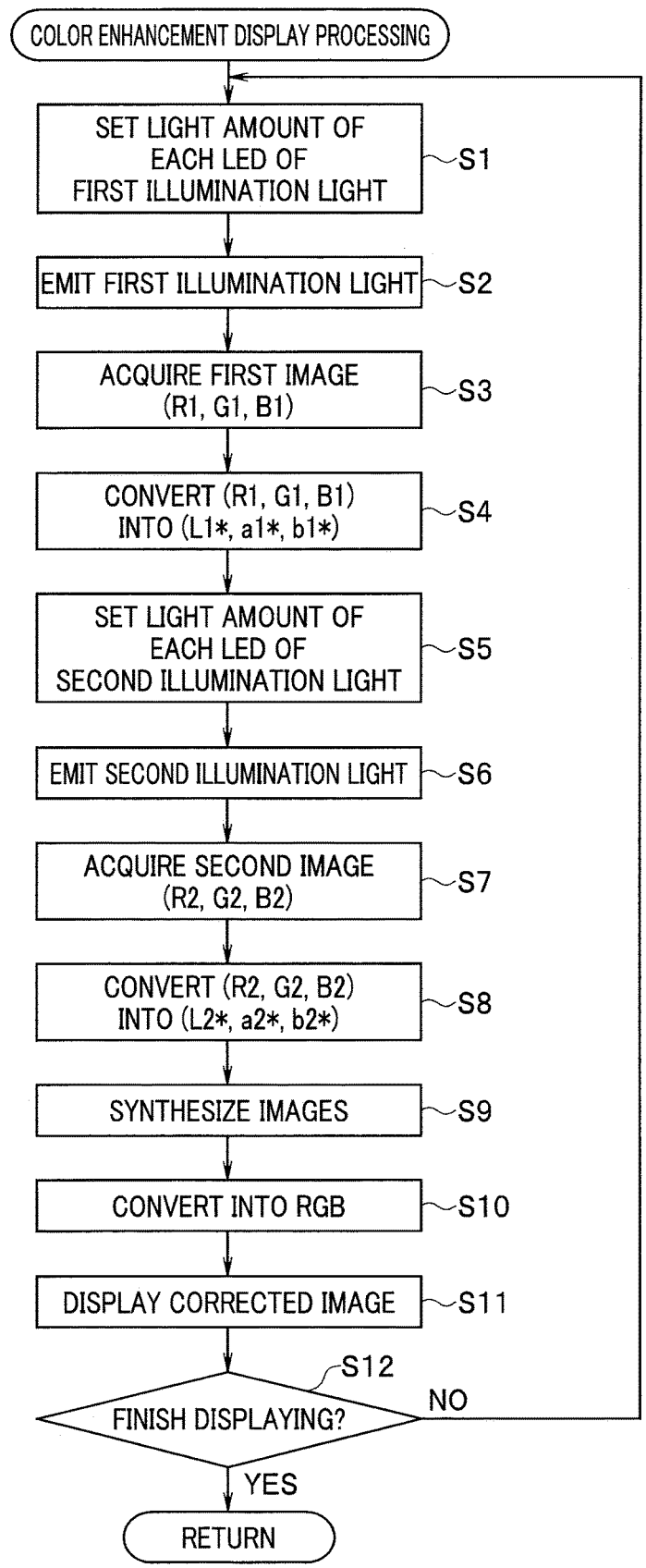
FIG. 3 is a flowchart illustrating color enhancement display processing to be performed by the endoscope apparatus according to the first embodiment.
Figure 5:
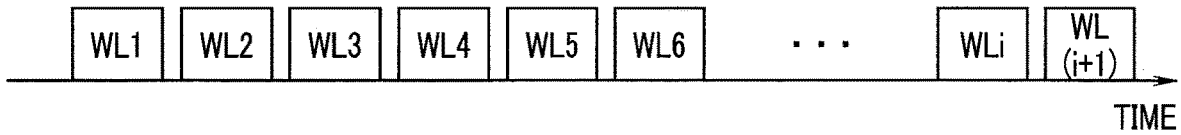
FIG. 5 is a timing chart indicating an example of an aspect where white light WL is emitted when the color enhancement mode is OFF according to the first embodiment.

FIG. 3 is a flowchart illustrating color enhancement display processing to be performed by the endoscope apparatus 1, FIG. 4 is a timing chart indicating an aspect where white light WL and color enhancement light CE are alternately emitted when the color enhancement mode is ON, and FIG. 5 is a timing chart indicating an example of an aspect where white light WL is emitted when the color enhancement mode is OFF.

Note that the color enhancement display processing illustrated in FIG. 3 is performed by the endoscope apparatus 1 when the color enhancement mode is ON in either the normal observation mode or the special light observation mode (here, the NBI observation mode).

As illustrated in FIG. 4, when the color enhancement mode is ON, the white light WL and the color enhancement light CE are alternately emitted for each one frame of image pickup. However, FIG. 4 merely illustrates an example, and light emission is not limited to the example in FIG. 4. For example, a modification may be made such that the color enhancement light CE corresponding to one frame is emitted after the white light WL corresponding to two frames is continuously emitted.

Note that while here, a case is assumed where color enhancement is performed by each combination of (WL1, CE1), (WL2, CE2), . . . , among the images picked up through radiation of respective kinds of illumination light illustrated in FIG. 4, color enhancement by each combination of (CE1, WL2), (CE2, WL3), . . . , may be further performed to improve an image pickup frame rate.

Further, when the color enhancement mode is OFF, the image pickup frame rate is preferably improved by emitting the white light WL also at light emission timings of the color enhancement light CE as illustrated in FIG. 5 instead of simply preventing emission of the color enhancement light CE. By improving the image pickup frame rate, a movie that can be easily observed can be generated even in a case where there is motion.

In main processing which is not illustrated, if the processing illustrated in FIG. 3 is started, the control unit 47 and the light source controller 31 set light amounts of the respective LEDs 32a to 32d to emit the first illumination light (step S1). Here, in an example where the first illumination light is white light WL (in a case of the normal observation mode), the light amounts of the respective LEDs 32a to 32d are set as follows.

FIG. 6 is a table indicating a setting example of the light amounts of the respective LEDs 32a to 32d in the first illumination light and the second illumination light when the color enhancement mode is ON in the normal observation mode.

The control unit 47 sets a light amount Gw of the green LED 32c in the white light WL based on the brightness information extracted from the image signal outputted from the A/D converter 41. Further, the control unit 47 reads color adjustment coefficients αwv, αwb and αwr for the white light WL from the memory 47a and multiplies the light amount Gw of the green LED 32c to respectively calculate a light amount Gv=αwv×Gw, of the violet LED 32a, a light amount Gb=αwb×Gw, of the blue LED 32b, and a light amount Gr=αwr×Gw, of the red LED 32d (see a field of WL in FIG. 6).

Note that in the present embodiment, by causing the violet LED 32a and the blue LED 32b to emit light at the same time, an image of return light from the subject, which is picked up by the B pixel of the image pickup device 21b, is obtained. The image of the return light is obtained in this manner to supplement the light amount of the blue LED 32b with the light amount of the violet LED 32a, and in the normal observation mode, the violet LED 32a is also substantially dealt with as an LED that emits blue light. However, if there is an enough light amount of the blue LED 32b, it is also possible to cause the blue LED 32b to emit light without causing the violet LED 32a to emit light and obtain return light from the subject by picking up an image with the B pixel.

The control unit 47 generates an illumination control signal with which the light amounts of the respective LEDs 32a to 32d set in this manner can be obtained and outputs the illumination control signal to the light source controller 31.

The light source apparatus 3 emits the first illumination light, here, for example, the white light WL by the light source controller 31 supplying a drive current to each semiconductor light emitting device based on the illumination control signal (step S2).

Then, the image pickup device 21b picks up an image of the return light from the subject to generate a first image pickup signal, and the processor 4 receives the first image pickup signal from the endoscope 2. The processor 4 processes the first image pickup signal by the preprocessing circuit 40 to the synchronization processing unit 43 to generate, for example, a first image signal (R1, G1, B1) having RGB components (step S3). The first image signal (R1, G1, B1) generated here is stored in the first memory 44a.

The L*a*b* conversion unit 44c reads the first image signal (R1, G1, B1) stored in the first memory 44a and converts the first image signal into a first image signal (L1*, a1*, b1*) of the L*a*b* color space (step S4).

Then, the control unit 47 and the light source controller 31 set light amounts of the respective LEDs 32a to 32d for emitting the second illumination light (step S5). Here, in a case where the first illumination light is the white light WL, the second illumination light is the color enhancement light CE related to the white light WL.

The control unit 47 sets the light amount of the green LED 32c in the color enhancement light CE to a light amount basically the same as the light amount Gw of the green LED 32c in the white light WL to prevent fluctuation of brightness (or luminance) of the first illumination light and the second illumination light.

However, when the light amount of the green LED 32c in the color enhancement light CE is set at Gw, in a case where at least one of the light amount of the violet LED 32a, the light amount of the blue LED 32b or the light amount of the red LED 32d to be calculated based on the second light amount ratio exceeds a maximum light amount of each kind of color light, the control unit 47 makes a setting so as to reduce the light amounts of the respective kinds of color light while maintaining the second light amount ratio so that all of the light amount of the violet LED 32a, the light amount of the blue LED 32b and the light amount of the red LED 32d become equal to or less than the maximum light amounts.

Thus, a color adjustment coefficient Kg illustrated in FIG. 6 is basically set at 1, and in a case where the second light amount ratio cannot be achieved with Kg=1, for example, the color adjustment coefficient Kg is set at a value Kg<1 as appropriate. Further, the light amount Gw of the green LED 32c in the white light WL is multiplied by the set Kg, and thereby a light amount Gw×Kg of the green LED 32c in the color enhancement light CE is calculated.

Further, the control unit 47 reads a color adjustment coefficient Kv related to the second light amount ratio from the memory 47a and multiplies the light amount αwv×Gw of the violet LED 32a in the white light WL to calculate the light amount Gv=αwv×Gw×Kv, of the violet LED 32a. Note that it goes without saying that the color adjustment coefficient Kv (and color adjustment coefficients Kb and Kr which will be described below) becomes different values in accordance with whether the color adjustment coefficient Kg is 1 or a value other than 1 to maintain the second light amount ratio.

In a similar manner, the control unit 47 reads the color adjustment coefficient Kb related to the second light amount ratio from the memory 47a and multiplies the light amount αwb×Gw of the blue LED 32b in the white light WL to calculate the light amount Gb=αwb×Gw×Kb, of the blue LED 32b.

The control unit 47 reads the color adjustment coefficient Kr related to the second light amount ratio from the memory 47a and multiplies the light amount αwr×Gw of the red LED 32d in the white light WL to calculate the light amount Gr=αwr×Gw×Kr, of the red LED 32d (see a field of CE in FIG. 6).

Here, the respective color adjustment coefficients Kg. Kv, Kb and Kr described above are obtained in advance as such coefficients that cause the second image signal to indicate achromatic color within a predetermined error range based on a spectral reflection factor of the reference portion of the subject, spectral sensitivity characteristics of the image pickup unit 21 and spectral light emission intensity characteristics of the light source unit 32 (for example, coefficients that makes an average of respective values of the R component, the G component and the B component the same within a predetermined error range) and are stored in the memory 47a.

It is assumed here that as the spectral reflection factor of the reference portion of the subject, a factor measured from a predetermined distance using the technique as disclosed in, for example, Japanese Patent Application Laid-Open Publication No. 2000-14629 (however, it is of course possible to apply other techniques as appropriate) is used.

Thus, values of the color adjustment coefficients Kg, Kv, Kb and Kr are typically different in accordance with combinations of the endoscope 2, the light source apparatus 3 and the processor 4, and thus, for example, the values may be stored in the memory 47a as a table in accordance with combinations of models.

Note that in a case where Kg=1, a specific example of the second light amount ratio is as follows.

$$V \text{ light}:B \text{ light}:G \text{ light}:R \text{ light}=(\alpha wv \times Kv):(\alpha wb \times Kb):1:(\alpha wr \times Kr)$$

Such a second light amount ratio may be changed in real time. For example, the control unit 47 may adjust the color adjustment coefficients Kv. Kb and Kr related to the second light amount ratio in real time so that an average of the respective signal values of the reference portion (an average will be expressed with < >) becomes <R2>=<G2>=<B2> within the predetermined error range in the second image signal (R2, G2, B2) of the RGB color space.

Alternatively, the control unit 47 may calculate an average <a2*> of a* components and an average <b2*> of b* components in the reference portion in the second image signal (L2*, a2*, b2*) of the L*a*b* color space and may adjust the color adjustment coefficients Kv, Kb and Kr in real time so that <a2*> and <b2*> become 0 within the predetermined error range.

For example, when <a*> is a positive value, a value of the color adjustment coefficient Kr is lowered, when <a*> is a negative value, the value of the color adjustment coefficient Kr is increased, when <b*> is a positive value, values of the color adjustment coefficients Kv and Kb are increased, and when <b*> is a negative value, the values of the color adjustment coefficients Kv and Kb are lowered. The reference portion in the second image signal may always be indicated in achromatic color within the predetermined error range by, for example, recursively performing such processing.

Alternatively, the following may be performed. First, a user such as a surgeon sets a normal portion which does not contain blood vessels, at a predetermined position where an average is to be calculated in the image by operating the endoscope 2. Then, the user operates the input device 6 to give an instruction to calculate an average at the predetermined position. This allows the user to select a portion which the user desires to be shown in achromatic color.

The control unit 47 generates the illumination control signal with which the set light amounts of the respective LEDs 32a to 32d can be obtained in this manner and outputs the illumination control signal to the light source controller 31.

The light source apparatus 3 emits second illumination light, here, the color enhancement light CE related to the white light WL based on the illumination control signal (step S6).

Then, the image pickup device 21b picks up an image of return light from the subject to generate a second image pickup signal, and the processor 4 receives the second image pickup signal from the endoscope 2. The processor 4 processes the second image pickup signal by the preprocessing circuit 40 to the synchronization processing unit 43 to generate, for example, a second image signal (R2, G2, B2) having RGB components (step S7). The second image signal (R2, G2, B2) generated here is stored in the second memory 44b.

The L*a*b* conversion unit 44c reads the second image signal (R2, G2, B2) stored in the second memory 44b and converts the second image signal into a second image signal (L2*, a2*, b2*) of the L*a*b* color space (step S8).

Then, the synthesis unit 44d synthesizes the first image signal (L1*, a1*, b1*) and the second image signal (L2*, a2*, b2*) for each pixel in the L*a*b* color space to generate a color enhanced corrected image signal (step S9).

Figure 10:
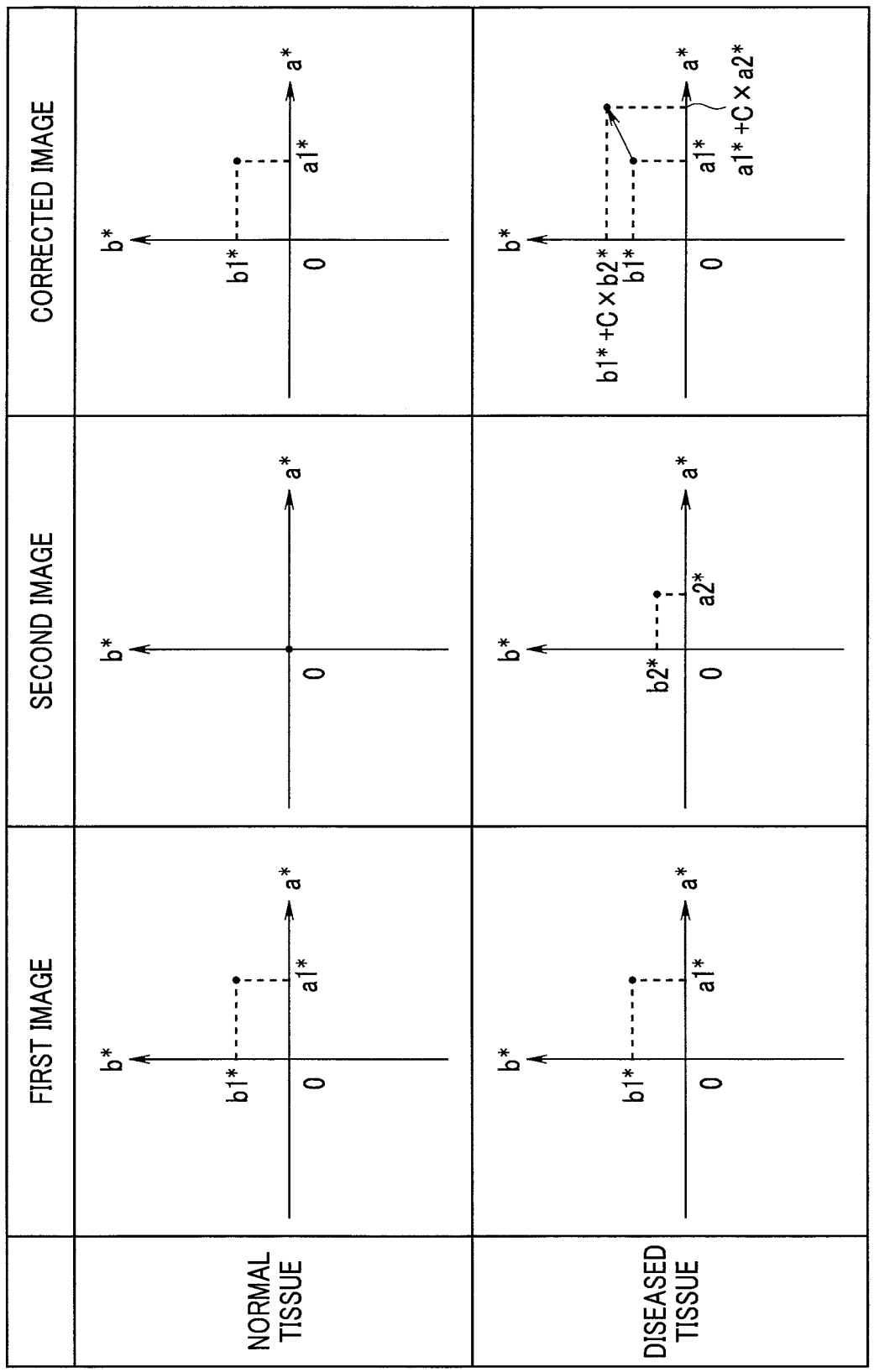
FIG. 10 is a table indicating an example of change of pixel signals of a pixel of a normal tissue and a pixel of a diseased tissue in a corrected image signal obtained by synthesizing a first image signal and a second image signal by a color enhancement unit according to the first embodiment.

FIG. 10 is a table indicating an example of change of pixel signals of a pixel of a normal tissue and a pixel of a diseased tissue in the corrected image signal obtained by synthesizing the first image signal and the second image signal by the color enhancement unit.

As described above, a normal tissue or the like which does not contain blood vessels is selected as the reference portion of the subject. In this case, as indicated in a field of the normal tissue in FIG. 10, the second illumination light is set so that the normal tissue in the second image is shown in achromatic color (gray scale such as white color), and thus, both values of the a* component and the b* component in the second image signal become 0 within the predetermined error range.

Thus, (as*, bs*) that is an a* component and an b* component of the synthesized corrected image signal does not change from the a* component and the b* component in the first image signal and is as indicated in Equation 1.

$$(as^*, bs^*) = (a1^*, b1^*) \quad \text{[Math. 1]}$$

In contrast, it is known that reflectance of blue band light to green band light of a diseased tissue, such as a body tissue including inflammation, is lower than reflectance of blue band light to green band light of a normal tissue (absorption of blue band light to green band light is increased). A signal of a pixel obtained by picking up an image of such a diseased tissue has a signal value in which R=G=B does not hold and becomes a signal value in which G<R and B<R.

In this manner, in a case of a diseased tissue, even if the portion is illuminated with the second illumination light, the portion is not shown in achromatic color (gray scale such as white color), and at least one of the a* component or the b* component of the second image signal has a value (a2*, b2*) other than 0.

The synthesis unit 44d calculates a component (as*, bs*) of the color enhanced corrected image signal as indicated in Equation 2 below by multiplying the component (a2*, b2*) of the second image signal by the enhancement coefficient C received from the control unit 47 and adding the result to the component (a1*, b1*) of the first image signal.

$$(as^*, bs^*) = (a1^* + C \times a2^*, b1^* + C \times b2^*) \quad \text{[Math. 2]}$$

While Equation 2 is also applied to a normal tissue in a similar manner, (a2*, b2*)=(0, 0) in the normal tissue, and thus, a result as indicated in Equation 1 is obtained. Further, if the enhancement coefficient C=1, a simple addition result of the component (a1*, b1*) of the first image signal and the component (a2*, b2*) of the second image signal becomes the component (as*, bs*) of the corrected image signal.

On the other hand, concerning an L* component (luminance component) of the corrected image signal, the synthesis unit 44d calculates Ls* that is the L* component of the synthesized corrected image signal by performing calculation, for example, as indicated in Equation 3 below using a second enhancement coefficient C2 received from the control unit 47.

$$Ls^* = L1^* + C2 \times (L2^* - L1^*) \quad \text{[Math. 3]}$$

The calculation in Equation 3 is correction by multiplying a difference value obtained by subtracting a luminance component L1* of the first image signal from a luminance component L2* of the second image signal by the second enhancement coefficient C2 and adding the result to the luminance component L1* of the first image signal.

As described above, in a case where a light amount of the green LED 32c in the color enhancement light CE is made the same as a light amount Gw of the green LED 32c in the white light WL, it is assumed that L1* becomes equal to or close to L2* and Ls* changes little from L1*.

Thus, in Equation 3, the luminance changes little, and mainly a color phase is enhanced by Equation 2.

Note that the synthesis method by the synthesis unit 44d is not limited to the above-described method, and other various kinds of methods can be applied.

Figure 11:
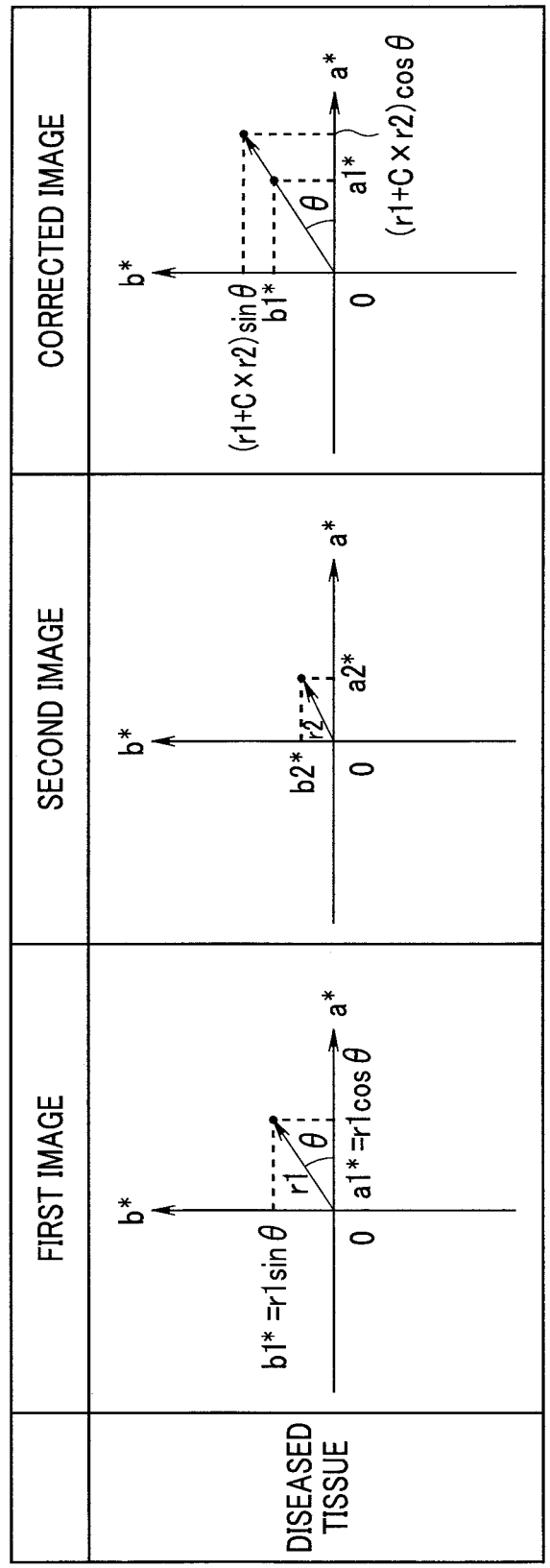
FIG. 11 is a table for explaining another example of a synthesis method by a synthesis unit according to the first embodiment.

FIG. 11 is a table for explaining other examples of the synthesis method by the synthesis unit 44d.

In the calculation method by Equation 2 described above, as indicated in a field of the diseased tissue and the corrected image in FIG. 10, while a color phase of the component (as*, bs*) of the corrected image signal is close to a color phase of the component (a1*, b1*) of the first image signal, some changes may occur in the color phase.

Thus, a synthesis method indicated in FIG. 11 is a method that does not cause change in a color phase.

A distance of the component (a1*, b1*) of the first image signal from an origin (0, 0) (that is, an L* axis) on an a*b* plane (L*=L1* plane) is set at r1 (see Equation 5 which will be described later), and an angle formed with an a* axis is set at θ.

In a similar manner, a distance of the component (a2*, b2*) of the second image signal from the origin (0, 0) on the a*b* plane (L*=L2* plane) is set at r2.

In this event, as indicated in Equation 4 below, the synthesis unit 44d calculates the component (as*, bs*) of the color enhanced corrected image signal by extending the distance r1 based on the distance r2 using the enhancement coefficient C received from the control unit 47.

$$(as^*, bs^*) = ([r1 + C \times r2] \cos \theta, [r1 + C \times r2] \sin \theta) \quad \text{[Math. 4]}$$

According to the calculation method indicated in Equation 4, the a*b* plane component of the second image signal is enhanced by the enhancement coefficient C and added to the a*b* plane component of the first image signal. Moreover, an angle formed by the component (as*, bs*) of the corrected image signal and the a* axis is the same as the angle θ formed by the component (a1*, b1*) of the first image signal and the a* axis, so that it is possible to perform color enhancement without changing a color phase.

Note that it is only necessary to calculate the L* component (luminance component) of the corrected image signal, for example, through calculation indicated in Equation 3 described above.

Still further, as the synthesis method by the synthesis unit 44d, a method of performing weighting addition on the component (a1*, b1*) of the first image signal and the component (a2*, b2*) of the second image signal may be used, in which case, weighting may be normalized. On the other hand, for the L* component, a value of the L1* component of the first image signal may be used as is as the L* component of the corrected image signal.

If the corrected image signal is generated by the synthesis unit 44d in this manner, the RGB conversion unit 44e converts the corrected image signal of the L*a*b* color space into a signal of the RGB color space and outputs the signal (step S10).

Then, the sharpness enhancement unit 45 performs sharpness enhancement processing, the display control unit 46 generates a video signal, and the color enhanced corrected image is displayed at the display 5 (step S11).

Then, the control unit 47 determines whether or not a setting of finishing the color enhancement display processing is made by an instruction signal from the input device 6 or the scope switch 23 (step S12), and in a case where the setting is not made, the processing returns to step S1, and the processing as described above is repeatedly performed.

On the other hand, in a case where it is determined in step S12 that the setting of finishing the color enhancement display processing is made, the processing returns to main processing which is not illustrated.

Note that while FIG. 6 indicates setting examples of the light amounts of the respective LEDs 32a to 32d in the second illumination light, a light amount ratio of the LEDs 32a to 32d may be changed in accordance with a portion of the subject. FIG. 7 is a table indicating an example of the normal observation mode in which the light amount ratio of the respective LEDs 32a to 32d in the second illumination light is made different in accordance with the portion of the subject.

In an example of a digestive tract, color of the reference portion of the subject differs in accordance with whether the portion of the subject is, for example, esophagus (first portion), stomach (second portion) or large intestine (third portion).

Thus, FIG. 7 is a table in which a color adjustment coefficient (Kv1, Kb1, Kr1) for the first portion, a color adjustment coefficient (Kv2, Kb2, Kr2) for the second portion, and a color adjustment coefficient (Kv3, Kb3, Kr3) for the third portion are prepared in advance as the color adjustment coefficient (Kv, Kb, Kr) and stored in the memory 47a of the control unit 47.

Here, as described above, the color adjustment coefficients for the respective portions are determined in advance as such coefficients that cause the second image signal to indicate achromatic color within the predetermined error range based on a spectral reflection factor of the reference portion of each portion measured using the technique as disclosed in, for example, Japanese Patent Application Laid-Open Publication No. 2000-14629, spectral sensitivity characteristics of the image pickup unit 21, and spectral light emission intensity characteristics of the light source unit 32.

Then, it is only necessary to select and use one of the color adjustment coefficients in accordance with the portion of the subject upon an examination. Here, the color adjustment coefficient may be selected by the user operating, for example, the input device 6 or the scope switch 23 to manually select the portion of the subject. Alternatively, it is also possible to determine the portion of the subject in the image through machine learning such as CNN (convolutional neural network) that has a successful record in image recognition and automatically select the color adjustment coefficient in accordance with the determination result.

Note that while a case where Kg=1 is assumed in FIG. 7, Kg #1 may be set as necessary in a similar manner to described above. In this case, a color adjustment coefficient such as Kg1, Kg2 and Kg3 different in accordance with the portion of the subject may be used. Here, Kg1 is a color adjustment coefficient to be multiplied by the light amount Gw of the white light WL in first color enhancement light (first CE) with which the first portion is to be irradiated, Kg2 is a color adjustment coefficient to be multiplied by the light amount Gw of the white light WL in second color enhancement light (second CE) with which the second portion is to be irradiated, and Kg3 is a color adjustment coefficient to be multiplied by the light amount Gw of the white light WL in third color enhancement light (third CE) with which the third portion is to be irradiated.

Further, FIG. 8 is a table indicating an example of the normal observation mode in which the light amount ratio of the respective LEDs 32a to 32d in the second illumination light is made different in accordance with the portion of the subject and in accordance with a distance from the distal end portion 2c of the endoscope 2 to the portion of the subject.

In a case where the distal end portion 2c of the endoscope 2 is close to the portion to be examined, the image pickup unit 21 can acquire the return light, as it is, from the subject irradiated with the illumination light emitted from the illumination optical system 22.

In contrast, in a case where the distal end portion 2c of the endoscope 2 becomes farther from the portion to be examined, there is a case where other portions are irradiated with return light from a certain portion as secondary light, and light incident on the image pickup unit 21 from the other portions includes return light of the illumination light and return light of the secondary light that are superimposed.

In this manner, there is a case where the light incident on the image pickup unit 21 from the subject is affected by reflected light and scattered light (hereinafter, multiple scattered light) including not only secondary light but also typically, higher-order light, in accordance with the distance to the subject.

Spectral components in a red wavelength band increases in the multiple scattered light in a living body, and thus, even if the same illumination light is radiated, the spectral reflection factor of the subject changes in accordance with the distance from the distal end portion 2c to the subject.

Thus, in the example, Kc1n for near distance, Kc1m for medium distance, and Kc1f for far distance are prepared in advance as the color adjustment coefficient Kc1 (where "c" indicates color, and c=v (violet), b (blue), r (red)) for the first portion in accordance with whether the distance from the distal end portion 2c of the endoscope 2 to the subject is a near distance, a medium distance or a far distance. In a similar manner, also for the color adjustment coefficients Kc2 and Kc3 for the second and the third portions, Kc2n for near distance, Kc2m for medium distance, Kc2f for far distance, Kc3n for near distance, Kc3m for medium distance, and Kc3f for far distance are prepared in advance.

Note that FIG. 8 is similar to described above in that Kg≠1 may be set, color "c" may include c=g (green), and Kg1n, Kg1m, Kg1f (the same also applies to cases of the second and the third portions) may be prepared in accordance with the distance to the subject.

It is only necessary to determine the color adjustment coefficient in accordance with the distance based on the spectral reflection factor of each portion measured in each of the near distance, the medium distance and the far distance using, for example, the technique as disclosed in Japanese Patent Application Laid-Open Publication No. 2000-14629 described above.

Specific examples of the determined color adjustment coefficient in a living body can include a color adjustment coefficient that lowers a light amount of the red LED 32*d* as the distance becomes farther, Kr1n>Kr1m>Kr1 f (the same applies to cases of the second and the third portions). Further, to prevent decrease in all the light amounts in association with decrease in the light amount of the red LED 32*d*, the respective light amounts of the green LED 32*c*, the violet LED 32*a* and the blue LED 32*b* may be slightly increased as the distance becomes farther.

Note that while the example has been described where the distance is divided into three stages of the near distance, the medium distance and the far distance, the distance may be divided into two stages or may be divided into four or more stages. Alternatively, the color adjustment coefficient corresponding to any distance may be obtained through interpolation.

The color adjustment coefficients prepared in this manner are stored in advance in the memory 47*a* of the control unit 47, and it is only necessary to select and use one of the color adjustment coefficients in accordance with the portion of the subject and the distance to the subject upon an examination. The selection in this event may be manually set by the user operating the input device 6 or the scope switch 23 or may be automatically set by the control unit 47 based on the distance measured with various kinds of techniques such as distance measurement using laser and distance measurement through image recognition, for example, concerning the distance.

Further, while in the above description, the color adjustment coefficient is made different in accordance with the distance as well as the portion of the subject, the color adjustment coefficient may be made different in accordance with an angle formed by a direction of the distal end portion 2*c* of the endoscope 2 and a direction formed by a plane of the portion of the subject in place of or in addition to the distance.

Further, while an example has been described above where the color enhancement mode is ON in the normal observation mode, as described above, in the endoscope apparatus 1 of the present embodiment, the color enhancement mode can be put into ON in the NBI observation mode. Here, flow of the color enhancement display processing in the NBI observation mode is similar to the flow indicated in FIG. 3 as described above.

FIG. 9 is a table indicating an example of the NBI observation mode in which a light amount ratio of the violet LED 32*a* and the green LED 32*c* in the second illumination light is made different in accordance with the portion of the subject.

The NBI observation mode is an observation mode in which light with two wavelengths, which is made a narrower band and which is easily absorbed by hemoglobin in the blood, specifically, as described above, violet light with a wavelength from 390 to 445 (nm) and green light with a wavelength from 530 to 550 (nm) is radiated, and capillary vessels in a superficial portion of the mucous membrane and a fine pattern of the mucous membrane are enhanced and displayed.

Thus, in the NBI observation mode, the violet LED 32*a* and the green LED 32*c* are made to emit light at a first light amount ratio to generate NBI illumination light as first illumination light.

Specifically, the control unit 47 calculates a light amount Gv=αNv×GN of the violet LED 32*a* by multiplying the light amount GN of the green LED 32*c* in the NBI illumination light by a color adjustment coefficient αNv for the NBI illumination light read from the memory 47*a* (see a field of NBI in FIG. 9) (step S1).

Then, the light source apparatus 3 emits the NBI illumination light of the set light amount (step S2), and the image pickup device 21*b* picks up an image of return light from the subject to generate a first image pickup signal. Upon the image pickup, a B pixel mainly picks up an image of return light of violet light, and a G pixel mainly picks up an image of return light of green light.

The synchronization processing unit 43 allocates the image signal related to the image pickup signal obtained from the B pixel to an R channel and a B channel, allocates the image signal related to the image pickup signal obtained from the G pixel to a G channel and performs synchronization processing (demosaicking processing) to generate, for example, a first image signal (R1. G1, B1) having RGB components (step S3).

The first image signal (R1, G1 B1) is stored in the first memory 44*a* and is converted into a first image signal (L1*, a1*, b1*) of the L*a*b* color space by the L*a*b* conversion unit 44*c* (step S4).

Then, the control unit 47 and the light source controller 31 set light amounts of the violet LED 32*a* and the green LED 32*c* for emitting the second illumination light (the color enhancement light CE related to the NBI illumination light) in the NBI observation mode (step S5).

First, the light amount of the green LED 32*c* in the color enhancement light CE is basically set to the same amount as the light amount GN of the green LED 32*c* in the NBI illumination light to prevent fluctuation of brightness (or luminance), in a similar manner to a case of the normal observation mode described above. Further, the light amount of the green LED 32*c* in the color enhancement light CE is changed as necessary to achieve the second light amount ratio, also in a similar manner to a case of the normal observation mode described above.

Further, the control unit 47 reads the color adjustment coefficient Kvx (where "x" indicates a number of the portion, x=1 in a case of the first portion, x=2 in a case of the second portion, and x=3 in a case of the third portion) related to the second light amount ratio from the memory 47*a* and calculates the light amount Gv=αNV×GN×Kvx of the violet LED 32*a* by multiplying the light amount αNv×GN of the violet LED 32*a* in the NBI illumination light (see fields of the first to the third CE in FIG. 9).

Here, the color adjustment coefficient Kvx is a coefficient such that color of the reference portion of the subject in the second image (R2, G2, B2) stored in the second memory 44*b* of the color enhancement unit 44 becomes achromatic color (gray scale such as white color), that is, (a2*, b2*)≈(0, 0).

Then, the light source apparatus 3 emits green light and violet light at the set second light amount ratio to thereby generate color enhancement light CE as the second illumination light (step S6).

The image pickup device 21b picks up an image of return light from the subject irradiated with the color enhancement light CE to generate the second image pickup signal. Upon the image pickup, the B pixel mainly picks up an image of return light of the violet light, and the G pixel mainly picks up an image of return light of the green light.

The synchronization processing unit 43 allocates the image signal related to the image pickup signal obtained from the B pixel to the R channel and the B channel, allocates the image signal related to the image pickup signal obtained from the G pixel to the G channel and performs synchronization processing (demosaicking processing) to generate a second image signal (R2, G2, B2) (step S7).

The second image signal (R2, G2, B2) is stored in the second memory 44b and converted into a second image signal (L2*, a2*, b2*) of the L*a*b* color space by the L*a*b* conversion unit 44c (step S8).

Then, the synthesis unit 44d synthesizes the first image signal (L1*, a1*, b1*) and the second image signal (L2*, a2*, b2*) using one of the methods described above regarding the normal observation mode to generate a color enhanced corrected image signal (step S9).

If the corrected image signal is generated by the synthesis unit 44d in this manner, the RGB conversion unit 44e converts the corrected image signal of the L*a*b* color space into a signal of the RGB color space and outputs the signal (step S10).

Then, the sharpness enhancement unit 45 performs sharpness enhancement processing, and the display control unit 46 generates a video signal. When the display control unit 46 generates the video signal, the display control unit 46 performs pseudo color processing of allocating the image signal of the G channel to the R channel and allocating the image signal of the B channel to the G channel and the B channel. The corrected image in the NBI observation mode, for which color is enhanced with the video signal generated in this manner is displayed at the display 5 (step S11).

Then, whether or not the processing is finished is determined (step S12), and in a case where the processing is not finished, the processing returns to step S1, and in a case where the processing is finished, the processing returns to main processing which is not illustrated, as described above.

Note that while FIG. 9 indicates an example where the color adjustment coefficient Kvx is made different in accordance with the portion of the subject, as described with reference to FIG. 8, the color adjustment coefficient Kv may be made different in accordance with a distance and an angle.

Further, while in the above description, NBI illumination is performed with a combination of the violet LED 32a and the green LED 32c, for example, an amber LED that emits amber light may be additionally provided (so-called a configuration of five LEDs) within the light source apparatus 3 to perform second NBI illumination.

In this case, the control unit 47 only requires to control the light source apparatus 3 to emit red light, green light and amber light at a first light amount ratio to thereby generate the second NBI illumination light (first illumination light) and emit red light, green light and amber light at a second light amount ratio to thereby generate color enhancement light as the second illumination light.

Further, color enhancement may be performed in a similar manner to that described above also in the special light observation mode such as an infrared observation mode and a fluorescent observation mode, as well as the NBI observation mode.

Figure 12:
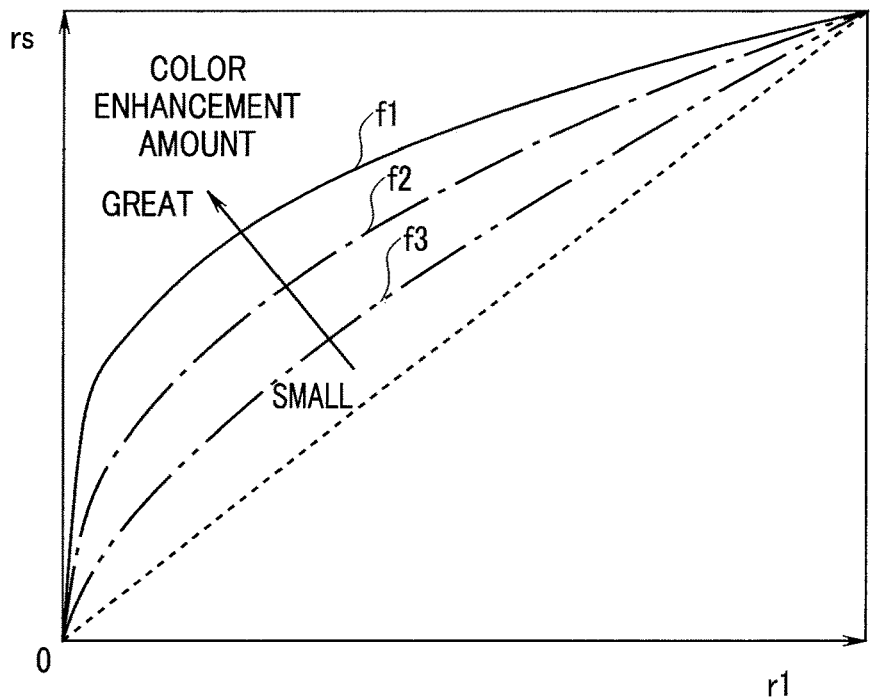
FIG. 12 is a graph indicating an example where a color enhancement amount is made to change in accordance with a distance of a component of the first image signal from an L* axis in an a*b* plane according to the first embodiment.

FIG. 12 is a graph indicating an example where a color enhancement amount is changed in accordance with a distance of the component (a1*, b1*) of the first image signal on the a*b* plane from the L* axis.

For example, if color enhancement is performed on the component (a1*, b1*) of the first image signal at a constant color enhancement amount, there is a case where color enhancement becomes excessive in a region where intensity is high, and the calculated value may exceed a feasible color range.

Thus, as indicated in FIG. 12, the color enhancement amount is preferably changed in accordance with the distance of the component (a1*, b1*) of the first image signal from the L* axis.

First, the distance of the component (a1*, b1*) of the first image signal from the L* axis is calculated as indicated in Equation 5 below as the distance r1 from the origin (0, 0) on the a*b* plane.

$$r1 = \sqrt{a1^{*2} + b1^{*2}} \quad \text{[Math. 5]}$$

In a similar manner, the distance of the component (as*, bs*) of the corrected image signal from the L* axis is calculated as indicated in Equation 6 below as the distance rs from the origin (0, 0) on the a*b* plane.

$$rs = \sqrt{as^{*2} + bs^{*2}} \quad \text{[Math. 6]}$$

A straight dotted line in FIG. 12 indicates a case where the distance rs is equal to the distance r1, and color enhancement is not performed.

On the other hand, functions f1 to f3 indicated in FIG. 12 indicate some examples of a function f that performs color enhancement in accordance with the distance r1. The function f is expressed, for example, as indicated in Equation 7 below using a constant k (0<k) and γ (0<γ<1) representing an exponent.

$$rs = f(r1) = k \cdot r1^{\gamma} \quad \text{[Math. 7]}$$

Here, γ representing an exponent mainly determines a curved shape of the function f, and if a value of γ is close to 1, the color enhancement amount becomes small as indicated in the function f3 of a dashed-two dotted line, if the value of γ is close to 0, the color enhancement amount becomes large as indicated in the function f1 of a solid line, and if the value of γ is medium, the color enhancement amount becomes medium as indicated in the function f2 of a dashed-dotted line. In other words, if γ of the function f1 is set at γ1, γ of the function f2 is set at γ2, and γ of the function f3 is set at γ3, a relationship of 0<γ1<γ2<γ3<1 holds.

Then, in the examples of all of the functions f1 to f3, the processor 4 sets the enhancement coefficient C so that the enhancement coefficient C monotonously decreases to gradually come closer to 0 in accordance with increase in the distance r1 from the L* axis on the a*b* plane.

Setting methods of the enhancement coefficient C as indicated in the functions f1 to f3 may be prepared in advance, and, for example, the user may select a setting method with which a desired color enhancement amount can be obtained.

Further, as indicated in an upper right corner in the graph in FIG. 12, a maximum value of the distance r1 is equal to a maximum value of the distance rs, and thus, even if color enhancement is performed using the method indicated in FIG. 12, a feasible color range is not exceeded.

Thus, by changing the enhancement coefficient C with the setting method as indicated in FIG. 12, it is possible to effectively perform color enhancement in a region where intensity is low while preventing color enhancement from becoming excessive in a region where intensity is high in the color space.

Figure 13:
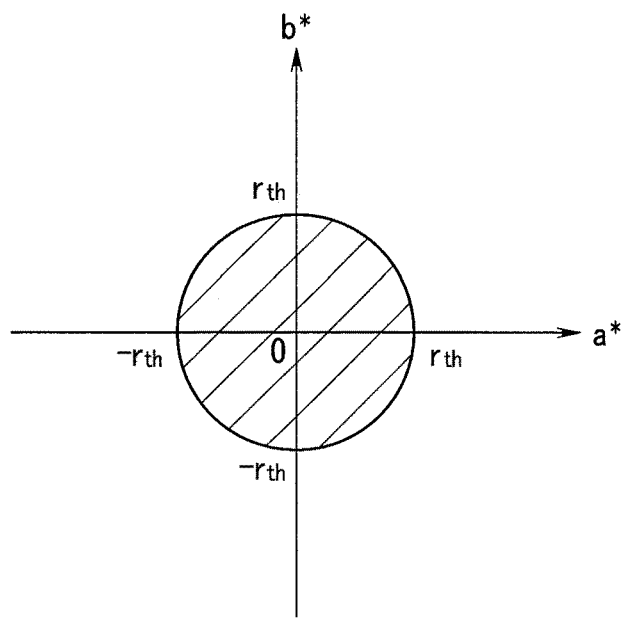
FIG. 13 is a graph indicating an example of a region in which color enhancement is to be performed in the a*b* plane according to the first embodiment.

Next, FIG. 13 is a graph indicating an example of a region where color enhancement is to be performed on the a*b* plane.

As indicated in FIG. 13, the region where color enhancement is to be performed on the a*b* plane may be limited to a constant range.

In other words, while color enhancement is performed on a pixel (pixel for which the component (a1*, b1*) falls within a hatched region indicated in FIG. 13) for which the distance r1 of the component (a1*, b1*) of the first image signal from the origin (0, 0) on the a*b* plane is less than a predetermined distance rth, color enhancement is not performed on a pixel for which the distance r1 is equal to or greater than the predetermined distance rth, and the component (a1*, b1*) of the first image signal is used as is as the component (as*, bs*) of the corrected image signal. Note that in this event, smoothing processing is preferably performed to prevent the color enhancement amount from rapidly changing in the distance r1=rth.

Note that while in the above description, the same enhancement coefficient C is used as the enhancement coefficient for the a* component and the enhancement coefficient for the b* component, the enhancement coefficients are not limited to these, and different enhancement coefficients may be set for the a* component and the b* component.

According to such a first embodiment, the first image signal related to the first illumination light for observing the subject is generated, the second image signal related to the second illumination light with which the reference portion of the subject is shown in achromatic color is generated, and color enhancement is performed based on the first image signal and the second image signal, so that it is possible to perform display while enhancing a slight difference in color without degrading color reproducibility.

In this event, in the second image signal, a portion with a spectral reflection factor different from a spectral reflection factor of the reference portion is not shown in achromatic color and has color, so that it is possible to perform color enhancement based on a difference in color through simple processing of adding the second image signal to the first image signal.

Further, color enhancement is performed using the second image signal acquired through radiation of the second illumination light, so that it is possible to prevent occurrence of artifacts depending on an image processing condition unlike with a case where color enhancement is performed by image processing being performed only on the first image signal.

Further, color enhancement is performed by converting the first image signal and the second image signal in such a way that signals of the RGB color space are converted into signals of the L*a*b* color space and respectively adding the a* component and the b* component of the second image signal to the a* component and the b* component of the first image signal, which separates the luminance component L*, so that it is possible to perform color enhancement while efficiently handling a color phase and intensity.

In this event, it is possible to control the color enhancement amount by multiplying the a* component and the b* component of the second image signal by the enhancement coefficient C and respectively adding the results to the a* component and the b* component of the first image signal.

Further, by setting the enhancement coefficient C so as to monotonously decrease to gradually come closer to 0 in accordance with increase of the distance r1 of the first image signal from the L* axis, it is possible to prevent color enhancement from becoming excessive in a region where intensity is high and effectively perform color enhancement in a region where intensity is low.

Further, it is possible to prevent color enhancement in a region where intensity is high by avoiding color enhancement in a case where the distance r1 of the first image signal from the L* axis is equal to or greater than the predetermined distance rth.

Then, by correcting the luminance component based on Equation 3, it is possible to obtain a luminance component of the corrected image signal having appropriate balance between luminance of the first image signal and luminance of the second image signal.

On the other hand, in a case where the distance r1 of the first image signal from the L* axis is extended based on the distance r2 of the second image signal from the L* axis using Equation 4, it is possible to perform color enhancement without changing a color phase.

Further, in a case where the color enhancement mode is ON using the white light WL as the first illumination light, an image of the normal observation mode, for which color is enhanced, can be observed.

In this event, the light amount of the green light in the second illumination light is made as close as possible to the light amount of the green light in the first illumination light, so that fluctuation of brightness (or luminance) can be prevented.

However, the light amount of each kind of color light is reduced within a range of a maximum light amount of each kind of color light as necessary while the second light amount ratio is maintained, and thus, even in a case where the light amount of the green light in the second illumination light cannot be made the same as the light amount of the green light in the first illumination light, the corrected image in which color is appropriately enhanced can be obtained.

Further, in a case where the color enhancement mode is ON using the NBI illumination light as the first illumination light, an image in the NBI observation mode, for which color is enhanced, can be observed. In this event, observation can be performed while color is enhanced in any of the NBI observation mode in which green light and violet light are combined, and the second NBI observation mode in which red light, green light and amber light are combined.

Then, by adjusting the second light amount ratio in real time, it is possible to always perform appropriate color enhancement on each frame of, for example, a movie.

Note that while an example of the CIE L*a*b* color space has been described in the above description, the color space is not limited to this, and other color coordinate systems may be used. As an example, a lightness color difference space YCrCb may be used. In this case, in the above description, it is only necessary to respectively replace L*, a* and b* with Y, Cr and Cb.

Note that while a case has been mainly described above where the present invention is an endoscope apparatus (endoscope system) including a processor, the present invention is not limited to this and may be a processing apparatus including a processor, a color enhancement method for performing color enhancement in a similar manner to the endoscope apparatus, a computer program for causing a computer to perform processing similar to the processing of the endoscope apparatus, a computer readable non-temporary recording medium that records the computer program, and the like.

Further, the present invention is not limited to the exact embodiment described above and can be embodied while modifying components within a range not deviating from the gist in an implementation stage. Further, various aspects of the invention can be formed by appropriately combining a plurality of components disclosed in the above-described embodiment. For example, some components may be deleted from all the components described in the embodiment. Further, components across different embodiments may be combined as appropriate. In this manner, various modifications and application can be performed within a range not deviating from the gist of the invention.

What is claimed is:

1. An endoscope system comprising:
an endoscope;
a light source apparatus; and
a processing apparatus, wherein
the light source apparatus includes a plurality of semiconductor light emitting devices configured to emit light with different center wavelengths and causes the plurality of semiconductor light emitting devices to emit light at a certain light amount ratio to generate illumination light,
the endoscope includes an image pickup device configured to pick up an image of return light from a subject irradiated with the illumination light to generate an image pickup signal having a plurality of color components,
the processing apparatus includes a processor,
the processor is configured to execute:
controlling the light source apparatus to switch light between first illumination light emitted at a first light amount ratio and second illumination light emitted at a second light amount ratio different from the first light amount ratio;
generating a first image signal based on an image pickup signal obtained by picking up an image of a subject illuminated with the first illumination light;
generating a second image signal based on an image pickup signal obtained by picking up an image of the subject illuminated with the second illumination light; and
generating a corrected image signal in which color is enhanced based on the first image signal and the second image signal, and
the second illumination light is light obtained by adjusting the second light amount ratio so that the second image signal related to a reference portion of the subject indicates achromatic color within a predetermined error range.

2. The endoscope system according to claim 1, wherein the processor
converts the first image signal and the second image signal in such a way that signals of an RGB color space are converted into signals of a CIE L*a*b* color space, and
enhances color of the first image signal by respectively adding an a* component and a b* component of the second image signal to an a* component and a b* component of the first image signal in the CIE L*a*b* color space.

3. The endoscope system according to claim 2, wherein the processor enhances color of the first image signal by multiplying the a* component and the b* component of the second image signal by an enhancement coefficient and then respectively adding the a* component and the b* component multiplied by the enhancement coefficient to the a* component and the b* component of the first image signal.

4. The endoscope system according to claim 3, wherein the processor sets the enhancement coefficient so that the enhancement coefficient monotonously decreases to gradually come closer to 0 in accordance with increase in a distance of the first image signal from an L* axis on an a*b* plane in the CIE L*a*b* color space.

5. The endoscope system according to claim 4, wherein the processor does not perform color enhancement in a case where the distance of the first image signal from the L* axis on the a*b* plane in the CIE L*a*b* color space is equal to or greater than a predetermined distance.

6. The endoscope system according to claim 3, wherein the processor further multiplies a difference value obtained by subtracting an L* component of the first image signal from an L* component of the second image signal by a second enhancement coefficient and adds the difference value multiplied by the second enhancement coefficient to the L* component of the first image signal.

7. The endoscope system according to claim 2, wherein both the a* component and the b* component in the second image signal are 0 within a predetermined error range.

8. The endoscope system according to claim 1, wherein the processor converts the first image signal and the second image signal in such a way that signals of an RGB color space are converted into signals of a CIE L*a*b* color space, and
enhances color of the first image signal by extending a distance of the first image signal from an L* axis on an a*b* plane based on a distance of the second image signal from the L* axis on the a*b* plane in the CIE L*a*b* color space.

9. The endoscope system according to claim 1, wherein the light source apparatus includes a semiconductor light emitting device configured to emit red light, a semiconductor light emitting device configured to emit green light, and a semiconductor light emitting device configured to emit blue light,
the processor controls the light source apparatus to:
generate white light as the first illumination light by causing red light, green light and blue light to be emitted at the first light amount ratio; and
generate color enhancement light as the second illumination light by causing red light, green light and blue light to be emitted at the second light amount ratio.

10. The endoscope system according to claim 9, wherein concerning a light amount of red light and a light amount of blue light calculated based on the second light amount ratio when a light amount of green light in the second illumination light is made same as a light amount of green light in the first illumination light,
the processor sets a light amount of green light in the second illumination light to a light amount that is the same as the light amount of the green light in the first illumination light in a case where both the light amount of the red light and the light amount of the blue light are equal to or less than a maximum light amount, and
makes a setting so as to reduce the light amounts of the green light, the red light and the blue light while maintaining the second light amount ratio so that both the light amount of the red light and the light amount of the blue light become equal to or less than the maximum light amount in a case where at least one of the light amount of the red light or the light amount of the blue light exceeds the maximum light amount.

11. The endoscope system according to claim 1, wherein the light source apparatus includes a semiconductor light emitting device configured to emit green light and a semiconductor light emitting device configured to emit violet light, and the processor controls the light source apparatus to:

cause NBI illumination light as the first illumination light to be generated by causing green light and violet light to be emitted at the first light amount ratio; and cause color enhancement light as the second illumination light to be generated by causing green light and violet light to be emitted at the second light amount ratio.

12. The endoscope system according to claim 1, wherein the light source apparatus includes a semiconductor light emitting device configured to emit red light, a semiconductor light emitting device configured to emit green light, and a semiconductor light emitting device configured to emit amber light, and the processor controls the light source apparatus to:

cause NBI illumination light as the first illumination light to be generated by causing red light, green light and amber light to be emitted at the first light amount ratio; and cause color enhancement light as the second illumination light to be generated by causing red light, green light and amber light to be emitted at the second light amount ratio.

13. The endoscope system according to claim 1, wherein the processor adjusts the second light amount ratio in real time so that the second image signal indicates achromatic color within a predetermined error range.

14. The endoscope system according to claim 1, wherein the second illumination light is set so that a normal tissue in the second image signal is shown in achromatic color.

15. A processing apparatus comprising:

a processor, wherein the processor is configured to execute:

controlling a light source apparatus to switch light between first illumination light in which a plurality of kinds of light with different center wavelengths are emitted at a first light amount ratio and second illumination light in which the plurality of kinds of light are emitted at a second light amount ratio different from the first light amount ratio;

generating a first image signal based on an image pickup signal obtained by picking up an image of a subject illuminated with the first illumination light;

generating a second image signal based on an image pickup signal obtained by picking up an image of the subject illuminated with the second illumination light; and generating a corrected image signal in which color is enhanced based on the first image signal and the second image signal, and the second illumination light is light obtained by adjusting the second light amount ratio so that the second image signal related to a reference portion of the subject indicates achromatic color within a predetermined error range.

16. A color enhancement method comprising:

emitting light while switching light between first illumination light in which a light amount ratio of a plurality of kinds of light with different center wavelengths is set at a first light amount ratio and second illumination light in which the light amount ratio is set at a second light amount ratio different from the first light amount ratio;

generating a first image signal based on an image pickup signal obtained by picking up an image of a subject illuminated with the first illumination light;

generating a second image signal based on an image pickup signal obtained by picking up an image of the subject illuminated with the second illumination light;

generating a corrected image signal in which color is enhanced based on the first image signal and the second image signal; and adjusting the second light amount ratio so that the second image signal related to a reference portion of the subject indicates achromatic color within a predetermined error range.

* * * * *